United States Patent [19]

Sherry et al.

[11] 4,379,143
[45] Apr. 5, 1983

[54] TOPICAL LIQUID OR OINTMENT

[75] Inventors: Howard S. Sherry, Cherry Hill, N.J.; Elliott P. Hertzenberg, Wilmington, Del.

[73] Assignee: PQ Corporation, Valley Forge, Pa.

[21] Appl. No.: 344,340

[22] Filed: Feb. 1, 1982

Related U.S. Application Data

[63] Continuation-in-part of Ser. No. 213,261, Dec. 5, 1980, abandoned.

[51] Int. Cl.³ ............................................. A61K 33/06
[52] U.S. Cl. ................................................... 424/154
[58] Field of Search ........................................ 424/154

Primary Examiner—Stanley J. Friedman
Attorney, Agent, or Firm—Ernest G. Posner; Fred C. Philpitt; J. Stephen Bobb

[57] ABSTRACT

Activated or partially activated zeolites can be included in analgesic balms or ointments as improved replacements for rubefacients. Upon hydration, the zeolite becomes warm, thereby helping to relieve pains associated with various musculoskeletal problems. An especially useful composition involves an ointment or balm that contains a combination of functional ingredients. A conventional analgesic such as a salicylate that can be absorbed through the skin supplies one form of relief that generally requires a period of time to become effective. When combined with the zeolite, which begins to hydrate at once, immediate relief is provided through the generated warmth.

11 Claims, No Drawings

TOPICAL LIQUID OR OINTMENT

This application is a continuation in part of our copending application Ser. No. 213,261 filed Dec. 5, 1980, allowed, but abandoned as of the filing date of this application.

BACKGROUND OF THE INVENTION

This invention relates to topical applications to relieve symptoms associated with mild muscle injuries and impaired joint function. In particular, the invention involves an analgesic balm, ointment, or liquid that contains activated zeolite as a functional source of heat.

Relief of symptoms associated with musculoskeletal distress can often be provided by local analgesics in the form of balms or ointments. In general, these compositions contain a number of ingredients, some of which are functional and others that simply act as vehicles for delivering the functional components. The functional ingredients often include pain relievers that can be absorbed through the skin for major pain relief, and a rubefacient. In general, the pain reliever requires some time to become effective, while the rubefacient acts very quickly to promote relief through warming. The rubefacient acts to dilate the vessels in the application area so that the area becomes warmer and the skin red. Examples of these materials as known in the present art include capsicum oleoresin, camphor, chloroform, menthol and allyl isothiocyanate. In general, the warming feature of these materials is somewhat fugitive and does not provide relief sustained until the action of the analgesic medicament becomes effective.

It is an object of this invention to provide an analgesic balm that causes a gentle sustained warming of the application area without the irritating effects of the usual rubefactients.

U.S. Pat. No. 3,250,680 discloses cosmetic compositions such as skin creams, hand creams, ointments, shampoos, toothpastes and the like that include solids that liberate heat upon adsorbing water. Synthetic aluminosilicates are among the solids disclosed.

SUMMARY OF THE INVENTION

Activated or partially activated zeolites can be used as improved ingredients in analgesic balms, ointments or lotions, essentially replacing the usual rubefacient. The dehydrated or partially dehydrated zeolites are easily dispersed in an anhydrous carrier or vehicle materials to provide compositions that are easily applied to the skin of humans. When applied, the zeolite hydrates by removing moisture from the skin and the atmosphere. Considerable heat is released as the zeolite hydrates, warming the application area. The warming effect may be sustained because the zeolite hydrates slowly as moisture becomes available by diffusion through the atmosphere and the skin, and diffusion through the liquid vehicle.

The small particle size zeolites also act to thicken the liquid components of the analgesic balm so that convenient formulation for the correct viscosity of the product is possible.

One of the most important aspects of our composition is that the generation and maintenance of the heat of hydration of the zeolite can be controlled by varying the character of the liquid vehicle. If a very quick release of heat is desired, a hydrophilic vehicle is used; if a slow, sustained heat release is desired, a hydrophobic vehicle is required. Intermediate and controlled performance can be introduced by altering the hydrophobic vehicle to provide some hydrophilic characteristics.

THE INVENTION

The zeolites that constitute the functional component of our invention can be naturally occurring and/or synthetic crystalline metal aluminosilicates. The chemical composition, structure, preparation, and physical and chemical properties of such zeolites have been disclosed in numerous articles, patents and texts. These sources include D. W. Breck's book, *Zeolite Molecular Sieves; Structure, Chemistry and Uses* (Wiley-Interscience: 1974). Synthetic zeolites are preferred for the compositions of our invention because they can be specially manufactured to provide any desired properties. Synthetic crystalline metal aluminosilicates such as those described in U.S. Pat. Nos. 2,882,243-4; 3,012,853; 3,130,007 and 3,329,621, among others, are suitable ingredients in our composition.

Such zeolites are prepared by combining aqueous solutions containing sources of silica, alumina and alkali to produce an alkaline aluminosilicate gel which crystallizes upon hydrothermal treatment. Washing and drying steps complete the preparation. Our application requires that the zeolite be dehydrated to a very low water content. The dehydration is accomplished by heating the zeolite at temperatures sufficient to completely eliminate the water, but below the decomposition point of the zeolite. Useful zeolites conform to the formula:

$$M_{x/n}[(AlO_2)_x(SiO_2)_y]$$

In this formula x and y are integers greater than 6, the molar ratio of x to y is 0.1 to 1.1 and M is a metal with the valence of n. Usually, zeolites are prepared in the sodium form. We can convert such materials to any substituted form we wish by ion exchange. The zeolites used in our composition must be activated. We consider a zeolite to be activated if it generates a substantial exotherm upon hydration. The zeolite should contain 5% water or less.

The other active ingredient in our composition includes any pain reliever that can be absorbed through the skin. The materials include, among others, methyl salicylate, glycol monosalicylate and triethyl amine salicylate.

The carrier or vehicle for the two active ingredients is important since it constitutes a large proportion of the composition. Said carrier or liquid vehicles must be largely anhydrous. In addition, the liquid vehicle should not penetrate into the cages of the zeolite and be absorbed. The absorption is accompanied by a release of heat, so that any substantial release of heat when the liquid vehicle and the zeolite are mixed would indicate that the combination should not be used. For example, when 25 g of Zeolite CaX is mixed with 25 g of glycerin a temperature rise of 59° C. from room temperature is noted, so this combination should not be used. Further evaluation of such combinations is disclosed in the examples. While most zeolites exhibit the exothermic reaction required for use in our composition, we prefer less siliceous materials that have smaller cages. We therefore most prefer zeolites of the A type to be used for the composition of our invention. The chemical composition of Zeolite A has been defined in the prior art cited herein.

The viscosity of the zeolite liquid vehicle combination must also be considered. The zeolite and liquid vehicle should not interact so strongly to produce high viscosities that a composition with sufficient zeolite to produce the desired heat cannot be made. For example, a combination of equal parts by weight (pbw) of Zeolite CaX and glycerin is too viscous to be useful. On the other hand, the zeolite should contribute thickening so that the composition has the desired consistency. Useful liquids for the vehicle or carrier include, among others, stearyl alcohol, glyceryl monostearate, stearic acid, petrolatum, mineral oil, methyl paraben, propyl paraben, triethanol amine, surfactants, glycerin, polyethylene glycol and the like. The vehicle or carrier should contain less than about 3% water, and preferably less than 1.5% water.

One of the most important aspects to be considered when selecting the liquid vehicle or carrier is the way in which the liquid interacts with water. If the liquid vehicle is hydrophilic, completely miscible with water, moisture becomes distributed throughout the liquid, the zeolite becomes hydrated and releases its heat very rapidly. If the liquid vehicle is hydrophobic, immiscible with water, moisture diffuses into the liquid slowly and the heat release is delayed but is sustained for a longer period of time. The heat released upon hydration of the zeolite can be controlled by changing the hydrophobic-hydrophilic nature of the liquid vehicle. For example, a hydrophobic vehicle could be modified by adding a surfactant to introduce more water compatibility. As the proportion of surfactant is increased, water diffuses faster in the liquid and the zeolite hydrates more quickly with a resultant faster release of heat.

The release of heat upon moisture addition to our composition can also be controlled by coating the zeolite with either a material that must be dissolved before water can enter the zeolite cage or a partially hydrophobic material that delays water intrusion into the cages.

A composition that creates heat can be formed by blending 1 to 6 parts by weight (pbw) of the activated zeolite with 4 to 9 pbw of the carrier or vehicle. A composition that contains two functional materials can be formed by blending 1 to 5 pbw of zeolite, 0.1 to 0.5 pbw of a salicylate analgesic and 5 to 9 pbw of the anhydrous carrier or vehicle.

EXAMPLES

The following examples illustrate certain embodiments of the invention and should not be considered as establishing the scope of the invention. All proportions are in parts by weight (pbw) or percent by weight (%) unless otherwise stated.

Viscosity was measured with a Brookfield Viscometer, RVT model, using an appropriate spindle and rpm setting. A Number 3 or 4 spindle was used for most measurements. The viscosity measurements were done at a room temperature of 21±1° C.

The temperature change upon mixing water with the balm was measured as follows:
1. Weigh 50 g zeolite-liquid vehicle combination into a 150 ml beaker.
2. Note the temperature of the balm candidate.
3. Add the chosen amount of water and stir by hand for 30 seconds with a mercury thermometer.
4. Monitor the temperature with the thermometer; t=0 occurs at the time the water is first added to the balm.

EXAMPLE 1

An anhydrous ointment base was prepared; 6 pbw of the material was blended with 4 pbw of Zeolite CaA to produce a paste. The Zeolite CaA had a loss on ignition (LOI) of 2.2%. Three people spread a light coating of the paste on portions of their skin. A sustained release of heat was felt.

EXAMPLE 2

The same anhydrous ointment base (5 pbw) was blended with 5 pbw of Zeolite CaX to form a paste. This material also generated sustained warmth when placed on the skin. The Zeolite CaX had an LOI of 1.7%.

EXAMPLE 3

The same anhydrous ointment base (7 pbw) was blended with 3 pbw of Zeolite NaA to form a paste. This material also generated sustained warmth when placed on the skin. The Zeolite NaA had an LOI of 2.1%.

EXAMPLE 4

The suitability of various combinations of zeolite and liquid vehicles was tested by mixing equal parts by weight of each component and measuring the heat generated. The results are summarized in Table I.

TABLE I

| Heat Release Upon Mixing Activated Zeolite With a Carrier Liquid | | |
| --- | --- | --- |
| Activated Zeolite | Carrier Liquid | ΔT Max. Upon Mixing[1] |
| CaA | Glycerin | 3.0° C. |
| Na—A | Glycerin | 2.5° C. |
| CaX | Glycerin | 59.0° C. |
| Na—A | PEG-400[2] | 3.0° C. |
| CaX | PEG-400[2] | 11.0° C. |
| Na—A | Mineral Oil | 3.5° C. |
| CaX | Mineral Oil | 15.0° C. |

[1]25 g activated zeolite was mixed into 25 g carrier liquid in a 150 ml beaker. Temperatures were measured to the nearest 0.5° C.
[2]Polyethylene glycol with a molecular weight of 400.

These results indicate that various zeolites with the A structure can be suitably combined with liquid carriers that are useful in the composition of our invention.

EXAMPLE 5

The viscosities of various zeolite-liquid vehicle combinations were tested. The results are summarized in Table II.

TABLE II

| Viscosity of Zeolite-Liquid Vehicle Combinations | | | |
| --- | --- | --- | --- |
| Formulation | | Ratio | Viscosity |
| Zeolite | Carrier | (w/w) | (cp) |
| CaA | Glycerin | 40:60 | 5,100 |
| CaA | Glycerin | 50:50 | 138,000 |
| Na—A | Glycerin | 40:60 | 5,300 |
| CaX | Glycerin | 40:60 | 5,700 |
| CaA | PEG-400 | 40:60 | 2,400 |
| CaA | Mineral Oil | 40:60 | — |
| — | Glycerin | — | 1,350 |
| — | PEG-400 | — | 130 |
| — | Mineral Oil | — | 75 |

These results show that zeolites do increase the viscosity of the various liquid carriers to the useful range and that only Zeolite CaX of those tested appears to present some viscosity problem.

EXAMPLE 6

The heating effect of various zeolite-liquid vehicle combinations were tested by adding 5 g of water to 50 g of the zeolite-liquid vehicle combination as previously described. The results are summarized in Table III.

TABLE III

Heat Release Upon Mixing Zeolite-Liquid Vehicle Combinations

| Formulation | | | Temperatures Effect* | |
|---|---|---|---|---|
| Zeolite | Carrier | Ratio (w/w) | ΔT Max. (°C.) | Time at ΔT Max. (minutes) |
| CaA | Glycerin | 40:60 | 38.0 | 1.0 |
| CaA | Glycerin | 50:50 | 54.0 | 1.5 |
| Na—A | Glycerin | 40:60 | 35.5 | 1.0 |
| KA | Glycerin | 40:60 | 38.0 | 1.0 |
| CaX | Glycerin | 40:60 | 3.5 | 0.5 |
| CaA | PEG-400 | 40:60 | 48.0 | 0.5 |
| CaX | PEG-400 | 50:50 | 40.0 | — |
| CaA | Mineral Oil | 40:60 | 23.5 | 4.0 |
| — | Glycerin | — | 2.0 | 0.5 |
| — | PEG-400 | — | 7.5 | 0.5 |
| — | Mineral Oil | — | 0.5 | 1.0 |

*Temperature to nearest 0.5° C.; time to nearest 0.5 minute.

These results show that the zeolites that do not react with the liquid carrier have substantial temperature increases when they become hydrated. The results further show that the Zeolite CaX-glycerin combination does not release much heat.

EXAMPLE 7

Combinations of various zeolites (20 pbw) with glycerin (30 pbw) were mixed with 5 pbw of water and the change in temperature (ΔT) observed as a function of time. The results are summarized in Table IV.

TABLE IV

Temperature Change of Zeolite in Glycerin as a Function of Time (40 pbw zeolite, 60 pbw glycerin)

| | ΔT (°C.) | | | |
|---|---|---|---|---|
| Zeolite | 1 min | 5 min | 10 min | 15 min |
| CaA | 38 | 25 | 21 | 17 |
| NaA | 36 | 31 | 23 | 18 |
| KA | 39 | 28 | 20 | 16 |
| CaX | 4 | 4 | 4 | 4 |

These results show that the type A zeolites have a significant and sustained increase in temperature when hydrated, while the temperature rise of Zeolite CaX in glycerin is not significant.

EXAMPLE 8

Combinations of Zeolite CaA (20 pbw) and various liquid vehicles (30 pbw) were mixed with 5 pbw of water and the change in temperature (ΔT) observed as a function of time. The results are summarized in Table V.

TABLE V

Temperature Change of Zeolite CaA in Various Liquid Vehicles as a Function of Time (40 pbw Zeolite CaA, 60 pbw liquid)

| | ΔT (°C.) | | | | |
|---|---|---|---|---|---|
| Liquid Vehicle | 1 min | 5 min | 10 min | 15 min | 20 min |
| PEG-400 | 46 | 37 | 25 | 20 | 17 |
| Glycerin | 38 | 26 | 20 | 17 | — |
| Mineral Oil | 8 | 24 | 25 | 21 | 19 |

These results show that zeolites in combination with polyethylene glycol and glycerin which are completely water miscible release heat very quickly when mixed with water. This heating effect begins to dissipate but is still significant. The zeolite in mineral oil releases heat more slowly and in a sustained manner when mixed with water. This behavior results from the relative immiscibility of the mineral oil and water requiring the water to diffuse into the liquid vehicle prior to hydrating the zeolite.

We claim:

1. An analgesic preparation comprising 1 to 6 parts by weight of an activated zeolite of the formula:

$$M_{x/n}[(AlO_2)_x(SiO_2)_y]$$

wherein x and y are integers greater than 6, the molar ratio of x to y is 0.1 to 1.1 and M is a metal with the valence of n; and 4 to 9 parts of an anhydrous liquid wherein the zeolite is the sole warming ingredient.

2. The composition of claim 1 wherein the zeolite contains up to 5% water.

3. The composition of either of claims 1 or 2 wherein the anhydrous liquid is hydrophilic, hydrophobic or partially hydrophobic.

4. The composition of claim 3 wherein the zeolite is selected from the group consisting of Zeolite NaA, Zeolite KA, Zeolite CaA and mixtures thereof.

5. An analgesic preparation consisting essentially of 1 to 5 parts by weight of an activated zeolite of the formula:

$$M_{x/n}[(AlO_2)_x(SiO_2)_y]$$

wherein x and y are integers greater than 6, the molar ratio of x to y is 0.1 to 1.1 and M is a metal of valence n; 0.1 to 0.5 parts by weight of a salicylate analgesic and 5 to 9 parts by weight of an anhydrous liquid vehicle wherein the zeolite is the sole warming ingredient.

6. The composition of claim 5 wherein the zeolite contains up to 5% water.

7. The composition of either of claims 5 or 6 wherein the anhydrous liquid is hydrophilic, hydrophobic or partially hydrophobic.

8. The composition of claim 7 wherein the zeolite is selected from the group consisting of Zeolite NaA, Zeolite KA, Zeolite CaA and mixtures thereof.

9. An analgesic preparation comprising 1 to 6 parts by weight of an activated zeolite of the formula:

$$M_{x/n}[(AlO_2)_x(SiO_2)_y]$$

wherein x and y are integers greater than 6, the molar ratio of x to y is 0.1 to 1.1 and M is a metal with the valence of n; and 4 to 9 parts of an anhydrous hydrophobic liquid wherein the zeolite is the sole warming ingredient.

10. The composition of claim 9 wherein the zeolite contains up to 5% water.

11. The composition of claim 9 wherein the zeolite is selected from the group consisting of Zeolite NaA, Zeolite KA, Zeolite CaA and mixtures thereof.

* * * * *